US00PP15177P2

(12) United States Plant Patent
van Rijn

(10) Patent No.: US PP15,177 P2
(45) Date of Patent: Sep. 28, 2004

(54) ***ANTHURIUM* PLANT NAMED 'TRUE LOVE'**

(50) Latin Name: *Anthurium andreanum*
Varietal Denomination: True Love

(75) Inventor: Leonardus W. B. M. van Rijn, Schipluiden (NL)

(73) Assignee: Rijmplant B.V., Schipluiden (NL)

( * ) Notice: Subject to any disclaimer, the term of this patent is extended or adjusted under 35 U.S.C. 154(b) by 0 days.

(21) Appl. No.: 10/721,989

(22) Filed: Nov. 25, 2003

(51) Int. Cl.[7] ..... A01H 5/00
(52) U.S. Cl. ..... Plt./365
(58) Field of Search ..... Plt./365

*Primary Examiner*—Anne Marie Grunberg
(74) *Attorney, Agent, or Firm*—C. A. Whealy

(57) ABSTRACT

A new and distinct cultivar of *Anthurium* plant named 'True Love', characterized by its upright and outwardly spreading plant habit; freely clumping growth habit; durable dark green leaves; red-colored spathes with yellow orange-colored spadices that are positioned slightly above and beyond the foliage on strong and erect scapes; freely flowering habit; and good inflorescence longevity.

2 Drawing Sheets

Botanical classification/cultivar designation: *Anthurium andreanum* cultivar 'True Love'.

BACKGROUND OF THE INVENTION

The present invention relates to a new and distinct cultivar of *Anthurium* plant, botanically known as *Anthurium andreanum,* and hereinafter referred to by the name 'True Love'.

The new *Anthurium* is a product of a planned breeding program conducted by the Inventor in Schipluiden, The Netherlands. The objective of the program is to create and develop new compact, freely clumping and freely flowering *Anthurium* cultivars with strong roots, dark green leaves, attractive spathe color, and good inflorescence longevity.

The new *Anthurium* originated from a cross by the Inventor in 1999 of a proprietary selection of *Anthurium andreanum* identified as code number 9515, not patented, as the female, or seed, parent with a proprietary selection of *Anthurium andreanum* identified as code number 9715, not patented, as the male, or pollen, parent. The cultivar True Love was discovered and selected by the Inventor as a flowering plant within the progeny of the stated cross in a controlled environment in Schipluiden, The Netherlands in July, 2000.

Asexual propagation of the new cultivar by meristem culture in a laboratory in Belgium since July, 2000, has shown that the unique features of this new *Anthurium* plant are stable and reproduced true to type in successive generations of asexual propagation.

BRIEF SUMMARY OF THE INVENTION

The new *Anthurium* has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar 'True Love'. These characteristics in combination distinguish True Love as a new and distinct cultivar:

1. Upright and outwardly spreading plant habit.
2. Freely clumping growth habit.
3. Durable dark green leaves.
4. Red-colored spathes with yellow orange-colored spadices that are positioned slightly above and beyond the foliage on strong and erect scapes.
5. Freely flowering habit.
6. Good inflorescence longevity.

Plants of the new *Anthurium* can be compared to plants of the female parent, the proprietary selection identified as code number 9515. In side-by-side comparisons conducted in Schipluiden, The Netherlands, plants of the new *Anthurium* differed from plants of the selection 9515 in the following characteristics:

1. Plants of the new *Anthurium* were more compact than plants of the selection 9515.
2. Plants of the new *Anthurium* and the selection 9515 differed in spathe coloration as plants of the selection 9515 had white, red and green tri-colored spathes.

Plants of the new *Anthurium* can be compared to plants of the male parent, the selection 9715. In side-by-side comparisons conducted in Schipluiden, The Netherlands, plants of the new *Anthurium* differed from plants of the selection 9715 in the following characteristics:

1. Plants of the new *Anthurium* had darker green-colored leaves than plants of the selection 9715.
2. Plants of the new *Anthurium* and the selection 9715 differed in spathe coloration as plants of the selection 9715 had orange-colored spathes.

Plants of the new *Anthurium* can be compared to plants of the cultivar 'Red Love', disclosed in U.S. Plant Pat. No. 11,005. In side-by-side comparisons conducted in Schipluiden, The Netherlands, plants of the new *Anthurium* different from plants of the cultivar Red Love in the following characteristics:

1. Plants of the new *Anthurium* had flatter and fleshier leaves than plants of the cultivar Red Love.
2. Spathes of plants of the new *Anthurium* were flatter, thicker and more red in color than spathes of plants of the cultivar Red Love.
3. Spathes of plants of the new *Anthurium* turned green in color more slowly than spathes of plants of the cultivar 'Red Love'.

BRIEF DESCRIPTION OF THE PHOTOGRAPHS

The accompanying colored photographs illustrate the overall appearance of the new *Anthurium,* showing the colors as true as it is reasonably possible to obtain in colored reproductions of this type. Colors in the photographs may differ slightly from the color values cited in the detailed botanical description which accurately describe the colors of the new *Anthurium.*

The photograph on the first sheet comprises a side perspective view of a typical flowering plant of the cultivar 'True Love'.

The photograph on the second sheet comprises a close-up view of typical inflorescences of 'True Love'.

DETAILED BOTANICAL DESCRIPTION

In the following description, color references are made to The Royal Horticultural Society Colour Chart, 2001 Edition, except where general terms of ordinary dictionary significance are used. The aforementioned photographs and the following observations and measurements describe 10-month old plants grown in 14-cm containers in Schipluiden, The Netherlands, in a glass-covered greenhouse with average day temperatures of 23° C., average night temperatures of 21° C. and light levels about 6 kilolux.

Botanical classification: *Anthurium andreanum* cultivar True Love.

Parentage:

*Female parent.*—Proprietary selection of *Anthurium andreanum* identified as code number 9515, not patented.

*Male parent.*—Proprietary selection of *Anthurium andreanum* identified as code number 9715, not patented.

Propagation:

*Method.*—By meristem culture.

*Time to initiate roots on a meristem-cultured plant.*—About 28 days at 20 to 24° C.

*Time to develop roots on a meristem-cultured plant.*—About 270 days at 20 to 24° C.

*Root description.*—Thick, fleshy, dark pink to cream-colored; lateral roots, thick and abundant.

Plant description:

*Plant shape.*—Upright and outwardly spreading plant habit, broad inverted triangle, symmetrical.

*Growth habit.*—Freely clumping, bushy and dense growth habit; about nine clumps per plant. Appropriate for 14-cm containers; moderately vigorous.

*Plant height, from soil level to top of leaf plane.*—About 25 cm.

*Plant height, from soil level to top of inflorescences.*—About 30 cm.

*Plant diameter or spread.*—About 38 cm.

*Crop time.*—About ten months are usually required from planting of young plants to finished plants in a 14-cm container.

*Foliage description.*—Arrangement: Alternate; simple. Quantity per plant: About 45. Length: About 12.9 cm. Width: About 7.8 cm. Shape: Deltoid. Apex: Apiculate. Base: Cordate. Margin: Entire. Texture, upper and lower surfaces: Leathery; glabrous, smooth; durable. Venation pattern: Pinnate. Color: Developing leaves, upper surface: More green than 146A. Developing leaves, lower surface: 146A to 147B. Fully developed leaves, upper surface: Between 147A and 139A. Fully developed leaves, lower surface: 146B. Venation, upper surface: 146B. Venation, lower surface: 146C. Petiole: Length: About 15.7 cm. Diameter, just below geniculum: About 3.5 mm. Diameter, at plant base: About 4.5 mm. Texture: Smooth, glabrous. Color: 146B. Geniculum length: About 1.7 cm. Geniculum diameter: About 4 mm. Geniculum color: 146B. Wing length: About 1.8 cm. Wing diameter: About 4 mm. Wing color: 182C.

Inflorescence description:

*Inflorescence arrangement.*—Spathes with spadices held slightly above and beyond the foliage. Flowering structures arise from leaf axils. Freely and continuous flowering during the autumn in Schipluiden, The Netherlands. Typically about nine inflorescences per plant. Inflorescences not fragrant.

*Inflorescence longevity.*—Inflorescences last about two months under water conditions and about three months under summer conditions; inflorescences persistent.

*Spathe.*—Length: About 5.3 cm. Width: About 6.6 cm. Shape: Reinform with cordate tendencies. Apex: Abruptly acute to mucronulate. Base: Cordate. Margin: Entire. Texture, upper and lower surfaces: Leathery; glabrous, smooth. Aspect: Slightly cupped. Color: When opening, front surface: 46C; towards basal margins, 177C and 177D. When opening, back surface: 47B; towards basal margins, 177D. Fully developed, front surface: 46C. With development, color becoming closer to 53A to 53B; towards basal margins, 146A. Fully opened, back surface: 50A; towards basal margins, 51C.

*Spadix.*—Length: About 3.2 cm. Diameter: About 6 mm. Shape: Columnar, tapering towards the apex; apex, obtuse. Cross section: Rounded. Aspect: About 10° from vertical. Color: Immature: 17C; towards the apex, 17D. Mature: 27B to 27C; towards the apex, 23B to 23C.

*Flowers.*—Quantity per spadix: Numerous, about 150. Shape: Rounded. Height: Less than 0.5 mm. Diameter: About 0.8 mm.

*Reproductive organs.*—Androecium: Anther color: 11D. Amount of pollen: Scarce. Pollen color: 11C. Gynoecium: Stigma shape: Ovoid. Stigma color: N155D. Ovary color: N155D.

*Scape.*—Length: About 22.1 cm. Diameter: About 3 mm. Strength: Strong. Aspect: Erect to slightly outwardly slanted to about 30° from vertical. Color: 144A; towards the apex, 146B.

*Seed and fruit.*—Seed and fruit development has not been observed on plants of the new *Anthurium.*

Disease/pest resistance: Under commercial production conditions, plants of the new *Anthurium* have not been observed to be resistant to pathogens or pests common to *Anthurium.*

Temperature tolerance: Plants of the new *Anthurium* have been observed to tolerate temperatures from about 14 to 36° C.

It is claimed:

1. A new and distinct cultivar of *Anthurium* plant named 'True Love', as illustrated and described.

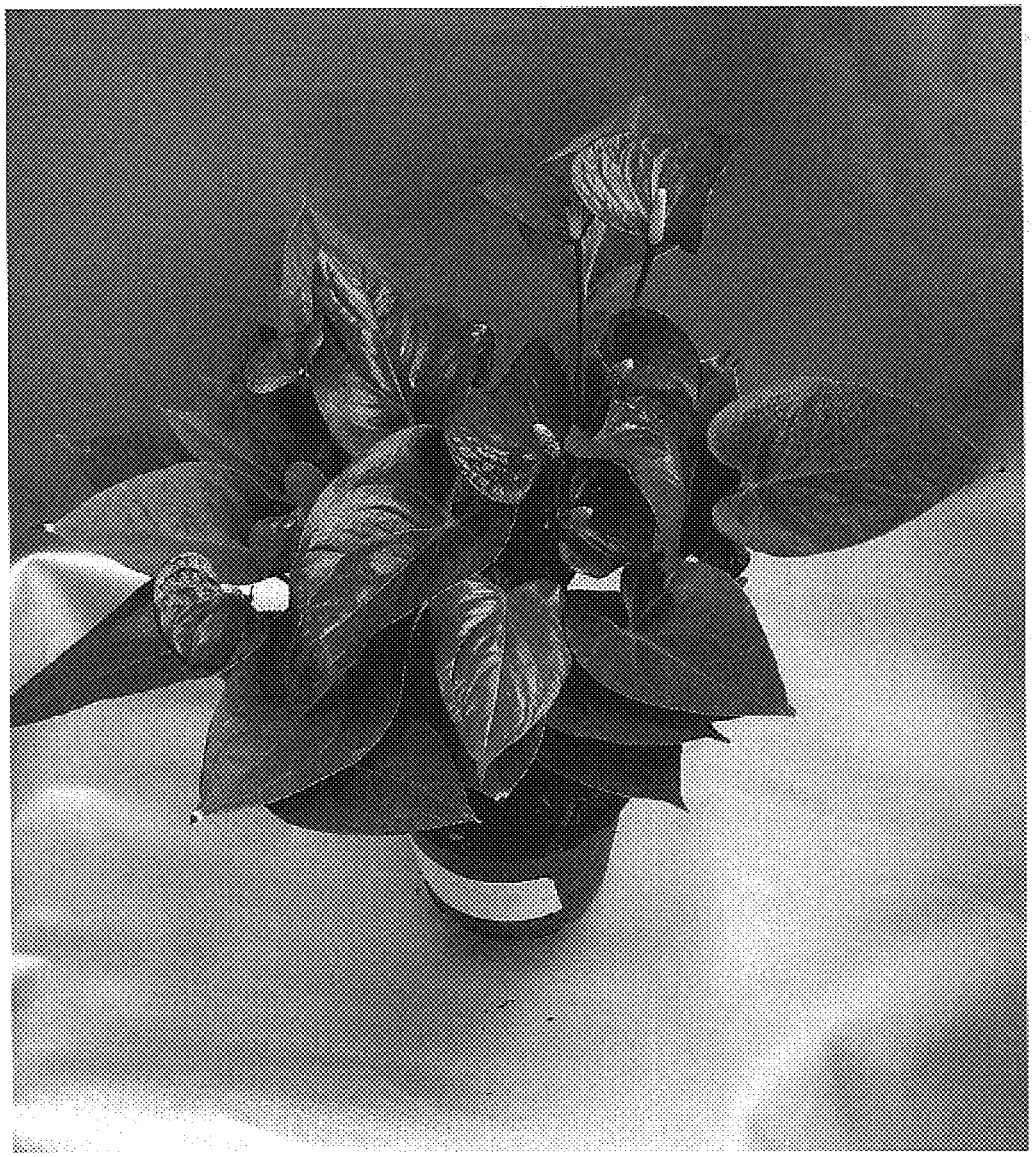

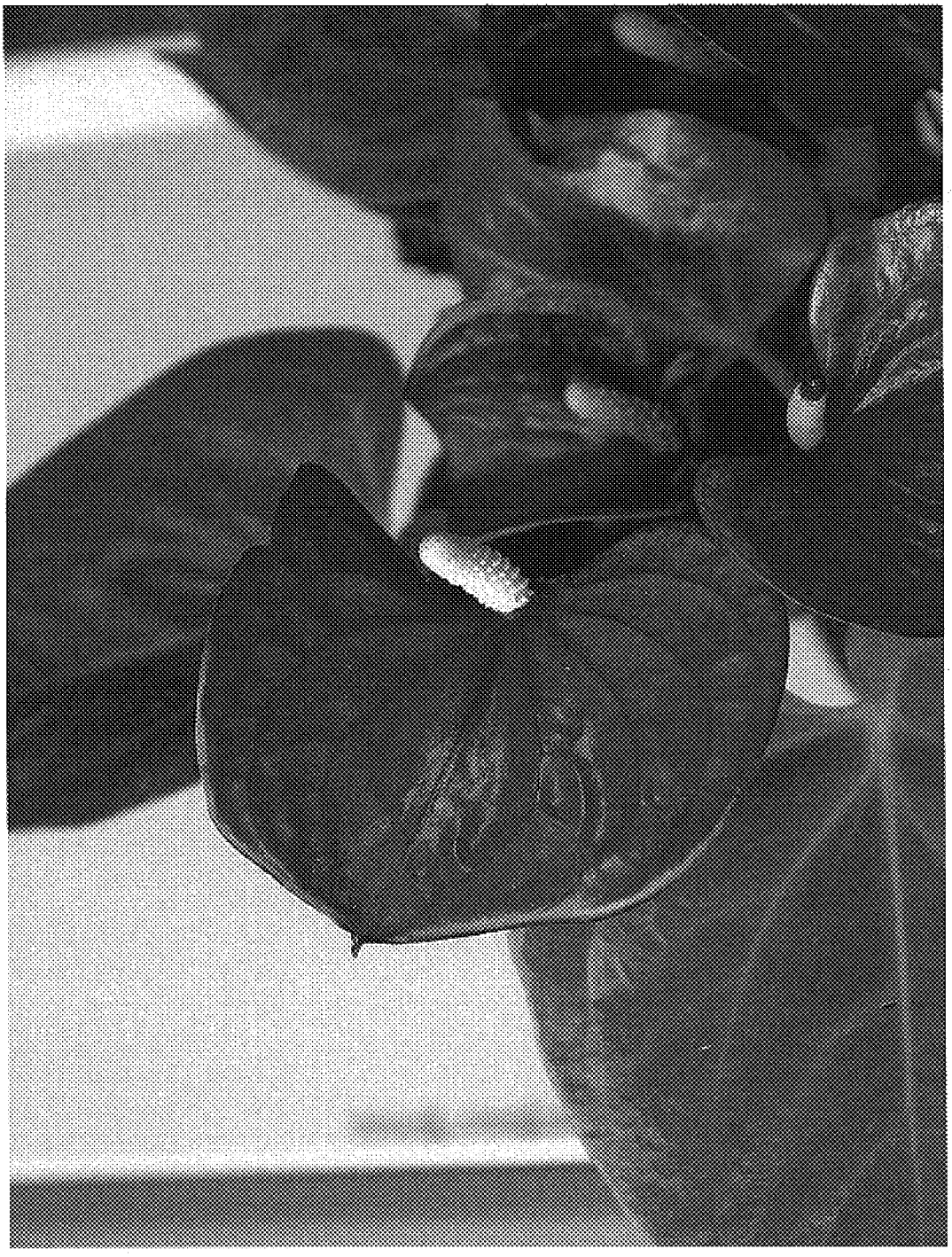

* * * * *